(12) United States Patent
Lechot et al.

(10) Patent No.: US 9,351,740 B2
(45) Date of Patent: *May 31, 2016

(54) ACETABULAR REAMER

(71) Applicant: Greatbatch Medical S.A., Orvin (CH)

(72) Inventors: Andre Lechot, Orvin (CH); Yves Desarzens, Corgemont (CH); Patrick M. White, Avondale, PA (US)

(73) Assignee: Greatbatch Medical S.A., Clarence, NY (US)

( * ) Notice: Subject to any disclaimer, the term of this patent is extended or adjusted under 35 U.S.C. 154(b) by 144 days.

This patent is subject to a terminal disclaimer.

(21) Appl. No.: 14/307,536

(22) Filed: Jun. 18, 2014

(65) Prior Publication Data

US 2014/0296857 A1    Oct. 2, 2014

Related U.S. Application Data

(60) Continuation of application No. 13/084,191, filed on Apr. 11, 2011, now Pat. No. 8,784,422, which is a division of application No. 10/266,442, filed on Oct. 8, 2002, now Pat. No. 7,922,721.

(60) Provisional application No. 60/328,154, filed on Oct. 9, 2001.

(51) Int. Cl.
*A61B 17/16*    (2006.01)

(52) U.S. Cl.
CPC ..... *A61B 17/1666* (2013.01); *A61B 2017/1602* (2013.01)

(58) Field of Classification Search
CPC ................................................. A61B 17/1666
USPC ............................................................ 606/80
See application file for complete search history.

(56) References Cited

U.S. PATENT DOCUMENTS

| 3,633,583 A |   | 1/1972  | Fishbein |
|---|---|---|---|
| 4,023,572 A | * | 5/1977  | Weigand et al. ................ 606/81 |
| 4,116,200 A | * | 9/1978  | Braun et al. .................... 606/81 |
| 4,239,427 A |   | 12/1980 | Walton |
| 5,302,234 A |   | 4/1994  | Grace et al. |
| 5,376,092 A |   | 12/1994 | Hein et al. |

(Continued)

FOREIGN PATENT DOCUMENTS

WO        9947051        9/1999

*Primary Examiner* — Samuel Hanna
(74) *Attorney, Agent, or Firm* — Michael F. Scalise

(57) ABSTRACT

An acetabular reaming system is disclosed of the type having a driver and a tool held together by a quick-release coupling mechanism. The tool (10) has a hollow body (12) defining a domed shape with a rotational axis (14), an apex (16) aligned with the axis (14) and a hemispherical wall (18) extending from the apex (16) to an equatorial rim (20) spaced 90 degrees from the axis (14). The rim (20) has an edge (22) visible to the user that indicates the position of the tool (10) relative to the bone. A first plurality of cutting sites (24) is arrayed along the body (12) and a second plurality of cutting sites (28) is arrayed circumferentially along the edge (22). Preferably, the first plurality of cutting sites (24) present raised first teeth (30, 130, 230, 330) having a profile selected from continuous squared (30), continuous rounded (130), discontinuous squared (230) and tongued (330) profiles. Also preferably, the second plurality of cutting sites (28) present raised second teeth (32, 132, 232, 332, 432) selected from continuous squared (32), continuous rounded (132), discontinuous squared (232), tongued (332) and bladed (432) profiles.

9 Claims, 5 Drawing Sheets

(56) References Cited

U.S. PATENT DOCUMENTS

| | | |
|---|---|---|
| 5,658,290 A | 8/1997 | Lechot |
| 5,755,719 A | 5/1998 | Frieze et al. |
| 5,817,096 A * | 10/1998 | Salyer .......................... 606/81 |
| 5,968,049 A | 10/1999 | Da Rold |
| 5,976,144 A | 11/1999 | Fishbein et al. |
| 5,980,170 A | 11/1999 | Salyer |
| 6,102,915 A | 8/2000 | Bresler et al. |
| 6,106,536 A * | 8/2000 | Lechot .......................... 606/180 |
| 6,129,732 A | 10/2000 | Lechot |
| 6,475,221 B1 | 11/2002 | White et al. |

* cited by examiner

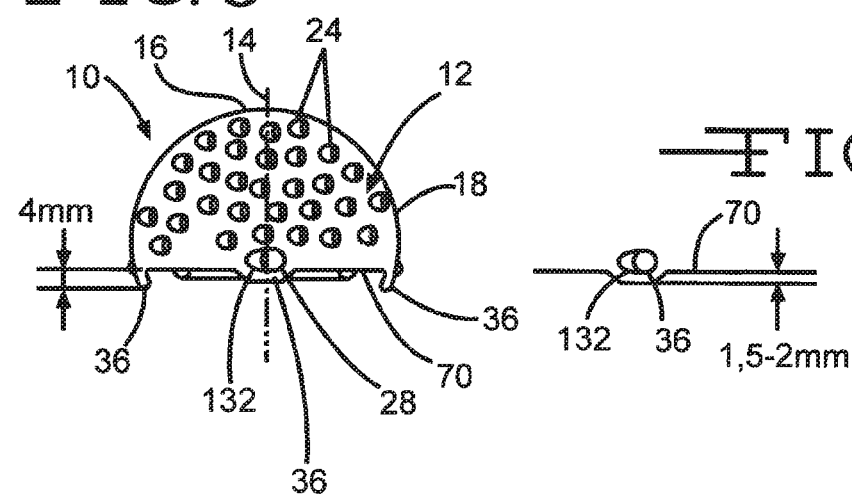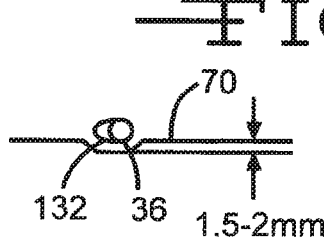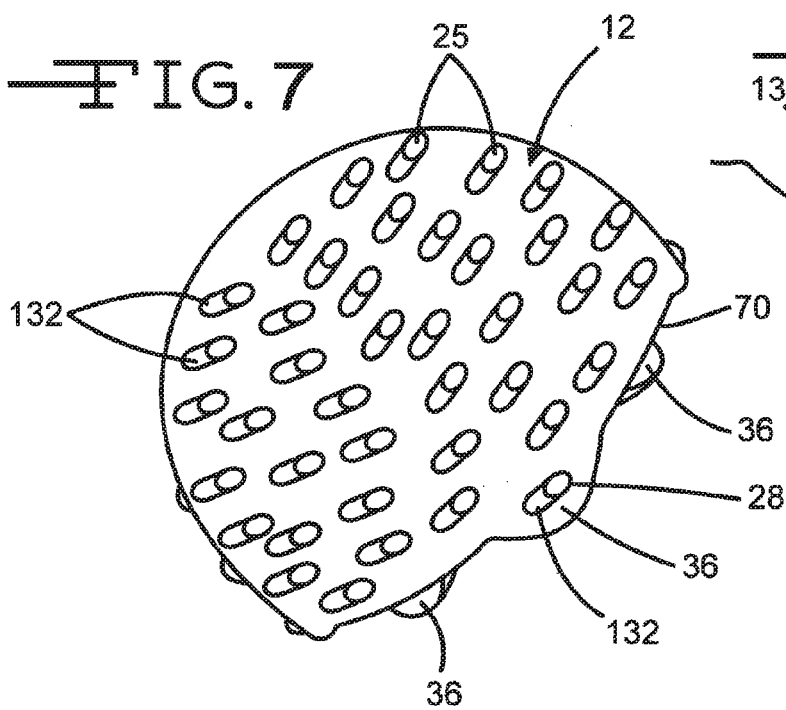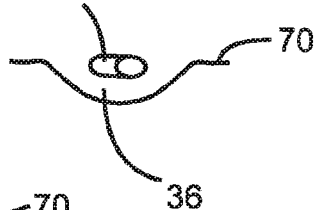

ACETABULAR REAMER

CROSS-REFERENCE TO RELATED APPLICATIONS

This application is a continuation of U.S. patent application Ser. No. 13/084,191, filed on Apr. 11, 2011, now U.S. Pat. No. 8,784,422, which is a divisional of U.S. patent application Ser. No. 10/266,442, filed on Oct. 8, 2002, now U.S. Pat. No. 7,922,721, which claims priority from U.S. provisional application Ser. No. 60/328,154, filed on Oct. 9, 2001.

TECHNICAL FIELD

The present invention relates to surgical cutting tools and instrumentation systems that utilize such tools, particularly tools having a domed shape for reaming a hemispherical bone cavity.

BACKGROUND

Acetabular reaming systems are well known in hip arthroplasty, to prepare bone tissue for receiving a hemispherical implant U.S. Pat. No. 5,658,290 to one of the present inventors, the entire contents of which are expressly incorporated by reference herein and relied-upon, discloses such a system. In the afore-mentioned patent, a surgical driver includes a quick disconnect mechanism having catches that receive a pair of orthogonal bars from a domed cutting tool.

It is highly desirable that the bone is shaped by the rotary tool into a cavity that conforms closely in hemispherical shape and dimension to the implant being received. Those skilled in the art have sought to provide rotary cutting tools that form the bone into a precise hemispherical cavity. It is further desirable to advance the tool linearly into the bone to fully cut the cavity, versus having to rock the tool sideways by changing its orientation to achieve a complete shape.

For example, one system has a tool with a cylindrical rim that continues parallel past the hemispherical equator of the tool, in order to allow presentation of teeth for a full cut. Such prior domed tools are referred to as "high-rim" reamers. Although these high-rim reamers have teeth presented for a straight-in (linear) advancement of cut into the cavity, there is no visual confirmation guiding the user to the finished cut. Actual position of the outer equatorial edge of the tool in the bone cavity is obscured and the user does not know exactly when to stop pushing in the tool.

Another type of tool is found in what is known as "hemispherical" reaming systems. These tools have no teeth presented for a full cut of the cavity simply by linear advancement of the tool into the bone. That is, a full, a straight-in cut is not possible hence the tool must be rocked sideways in order to present the teeth for cutting the final shape. This may result in over-cutting of the cavity.

Accordingly, a need exists for an improved reaming system wherein the user may precisely ascertain the swath being cut by the tool as it bottoms-out in the bone, to completely form the hemispherical-shaped cavity without the risk of overcutting. Particularly, there is a need for visual confirmation by the user of the position of the equatorial edge of the tool as the cavity is being fully cut.

There is also a need for an improved. reaming system wherein the tool is linearly advanced without having to "rock" the tool by changing the orientation of the cutting approach, in order to achieve a full cut.

There is a further need for a rotary cutting tool having a tooth design that precisely cuts a cavity with the desired size and shape of an implant to be received in the cavity, while employing a linear cut guided by accurate visual confirmation by the user.

SUMMARY OF INVENTION AND ADVANTAGES

According to an embodiment of the present invention, there is provided a tool for cutting a hemispherical cavity in bone. The tool is preferably part of a reaming system. that utilizes a driver with quick disconnect catches that receive mounting bars on the tool. The tool has a hollow body defining a domed shape with a rotational axis, an apex aligned with the axis and a hemispherical wall extending from the apex to an equatorial rim spaced 90 degrees from the axis. The rim has an edge visible to the user that indicates the position of the tool relative to the bone. A first plurality of cutting sites is arrayed along the body and at least one equatorial cutting site is located along the edge. Preferably the first cutting sites are open and the equatorial site closed.

In a preferred embodiment, the first plurality of cutting sites present raised first teeth having a profile selected from squared, rounded and tongued profiles.

In another preferred embodiment, the equatorial cutting site of the tool presents a raised second tooth selected from squared, rounded, tongued and bladed profiles.

According to another embodiment of the invention, the tool has a hollow body defining a domed shape with a rotational axis, an apex aligned with the axis and a hemispherical wall extending from the apex to an equatorial rim spaced 90 degrees from the axis. The rim has an edge visible to the user that indicates the position of the tool relative to the bone. A first plurality of cutting sites is arrayed along the body and a second plurality of cutting sites is arrayed circumferentially along the edge. Preferably, the first plurality of cutting sites present raised first teeth having a profile selected from squared, rounded and tongued profiles. Also preferably, the second plurality of cutting sites present raised second teeth selected from squared, rounded, tongued and bladed profiles.

According to yet another embodiment of the invention, the tool has a hollow body defining a domed shape with a rotational axis, an apex aligned with the axis and a hemispherical wall extending from the apex to an equatorial rim spaced 90 degrees from the axis. The rim has an edge visible to the user that indicates the position of the tool relative to the bone. A first plurality of cutting sites is arrayed along the body and a second plurality of cutting sites is arrayed circumferentially along the edge on downwardly depending lobes, which lobes preferably continue with substantially the same radius of curvature past the equator of the tool. Preferably, the first plurality of cutting sites present raised first teeth having a profile selected from squared, rounded and tongued profiles. Also preferably, the second plurality of cutting sites present raised second teeth selected from squared, rounded and tongued profiles.

In still another embodiment of the invention, the tool has a hollow body defining a domed shape with a rotational axis, an apex aligned with the axis and a hemispherical wall extending from the apex to an equatorial rim spaced 90 degrees from the axis. The rim has an edge visible to the user that indicates the position of the tool relative to the bone. At least one mounting bar, and preferably a pair of, mounting bars, extends across the underside of the body between diametrically opposed locations on the rim. A first plurality of cutting sites is arrayed along the body and a second plurality of cutting sites is outboard of the diametrically opposed. locations at the edge. Preferably, the second plurality of cutting sites is closed. It is also preferred that the second plurality of cutting sites present bladed teeth essentially extending outboard from the bars.

Thus, in one embodiment the present invention relates to a tool for cutting a hemispherical cavity in bone, comprising: a hemispherical, hollow dome extending from an apex to an equatorial rim, wherein a rotational axis central to the dome is aligned with the dome apex and wherein the equatorial rim is spaced from the rotational axis; at least one mounting bar extending perpendicular to the rotational axis with spaced apart ends secured to opposed locations of the dome; a plurality of first cutting teeth arrayed along the dome, but spaced form the equatorial rim thereof; at least two second cutting teeth, each second cutting tooth located at the equatorial rim and characterized as being a portion of the material of the dome having been raised in an upwardly direction to provide a second cutting edge of a cutting radii spaced further from the rotational axis than a hemispherical radii of the hemispherical dome to thereby interrupt the hemispherical continuity of the equatorial rim with the second cutting edge; and wherein the cutting radii and the hemispherical radii are each measured from a point where the rotational axis and an equatorial plane of the dome aligned perpendicular to the rotational axis meet.

An advantage of the present invention is the capability to perform an essentially perfect hemispherical cut, where the depth can be assessed clearly during the cut.

Another advantage of the invention is a tool presenting cutting sites that allow a full cut with clear visual confirmation while the user linearly advances the tool into the bone, without needing to change the orientation of the surgical driver and hence 'rock' the tool.

A further advantage of the invention is that, in preferred embodiments, the equatorial teeth are contained at closed cutting sites, which avoids risk of tissue entrapment.

Other objects and advantages will become apparent to a reader skilled in the art, with reference to the following Figures and accompanying Detailed Description wherein textual reference characters correspond to those denoted on the Drawings.

BRIEF DESCRIPTION OF THE DRAWINGS

FIG. 6 is an elevational view of a cutting tool of the present invention, showing equatorial cutting sites located on downwardly depending lobes, which contain rounded teeth;

FIG. 6A is a schematic view of a representative equatorial cutting site on a preferred downwardly depending lobe at the edge of the rim. of the body shown in FIG. 6;

FIG. 7 is a perspective view of FIG. 6;

FIG. 7A, is a schematic view of the equatorial tooth configuration shown in FIG. 7.

DETAILED DESCRIPTION

Figure 8:
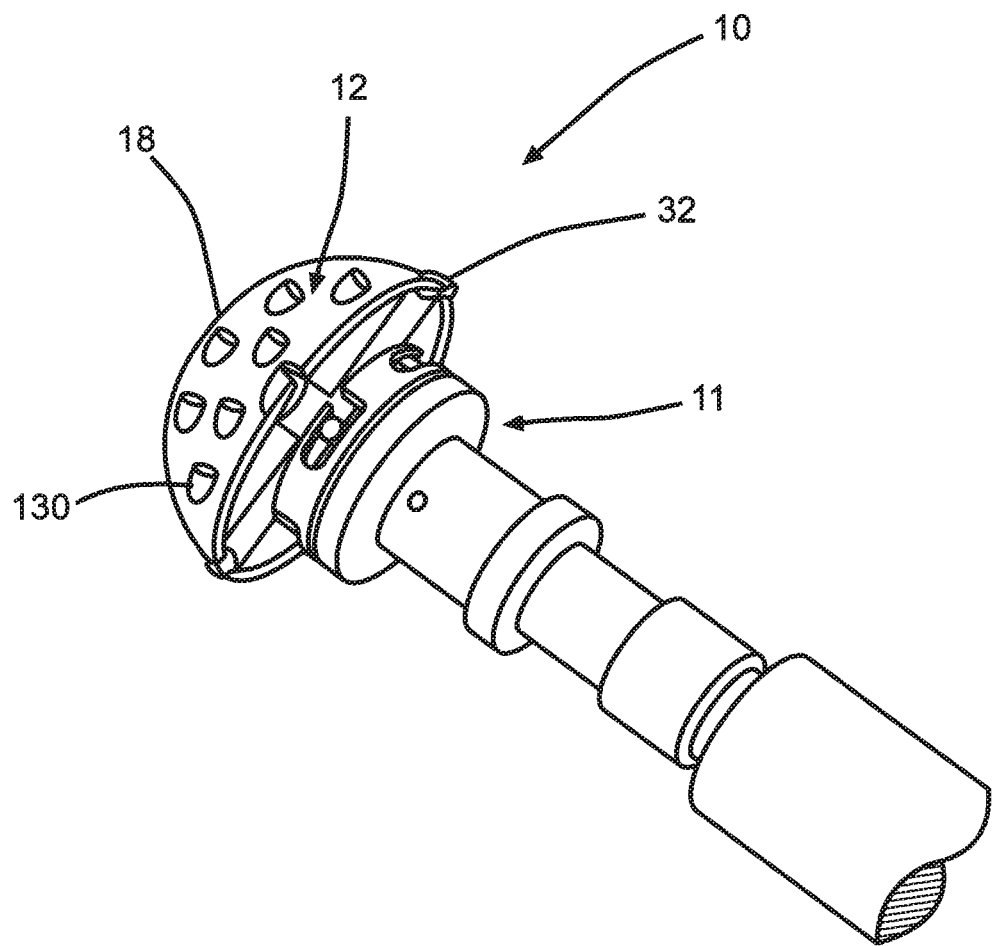
FIG. 8 is a perspective view of the reaming system of the invention, showing a tool and driver connected together and ready for use.

According to the present invention, there is provided a reaming system for cutting a hemispherical cavity in bone. Referring to FIGS. 1-7, the system has a tool 10 that utilizes a driver 11, shown in FIG. 8 with quick disconnect mechanism that receives the tool 10 for use. The structure and operation of driver 11 and its connecting mechanism is amply described in the aforementioned U.S. Pat. No. 5,658,290, which is essentially the same as the driver-tool mechanism shown by FIG. 8. Of course, other connecting mechanisms could be employed, such as a central boss provided on the tool, as described in WO 99/47051 of one of the present inventors. As shown by WO 99/47051, a single mounting bar could be used with one pair diametrically opposed ends, versus the pair of intersecting mounting bars shown in the '290 patent mentioned immediately above.

Figures 1, 1A:
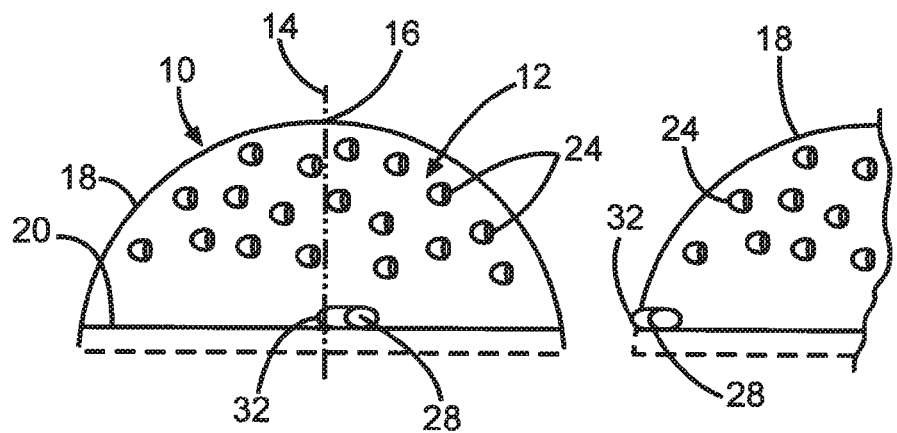
FIG. 1 is an elevational view of a tool of the present invention, showing an equatorial tooth with a preferred flattened profile.
FIG. 1A is a schematic view of the tooth configuration shown in FIG. 1.
Figures 2, 2A:
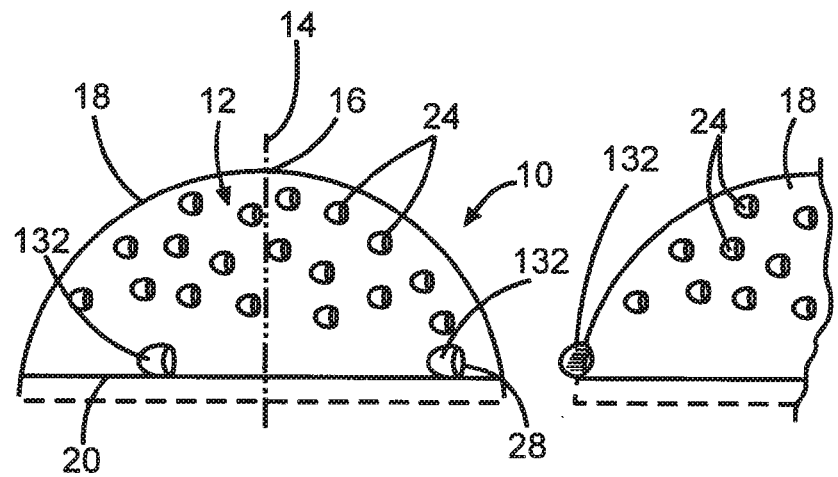
FIG. 2 is an elevational view of the tool of the of FIG. 1, showing an equatorial tooth with a preferred rounded profile.
FIG. 2A is a schematic view of the tooth configuration shown in FIG. 2.
Figures 3, 3A:
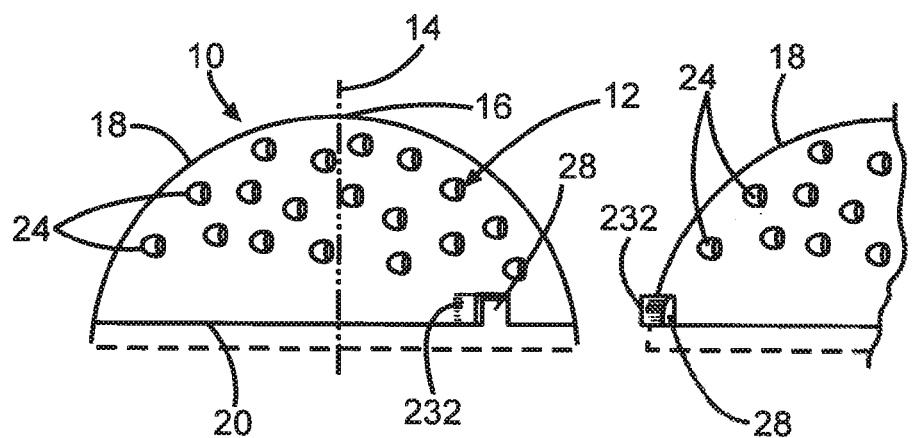
FIG. 3 is a perspective view of FIG. 1, showing an equatorial tooth with a preferred tongued profile.
FIG. 3A is a schematic view of the tooth configuration shown in FIG. 3.

Referring to FIGS. 1-3, the tool 10 has a hollow body 12 defining a domed shape with a rotational axis 14, an apex 16 aligned with the axis 14 and a hemispherical wall 18 extending from the apex 16 to an equatorial rim 20 spaced 90 degrees from the axis 14. The rim 20 has an edge 22 visible to the user that indicates the position of the tool 10 relative to the bone. A first plurality of cutting sites 24 is arrayed along the body 12 and at least one equatorial cutting site 28 is located along the edge 22.

Referring to FIGS. 1-7, the first plurality of cutting sites 24 present raised first teeth 30, 130, 230 preferably having a profile selected from squared 30 (FIGS. 4-5), rounded 130 (FIGS. 7-8) and tongued 232 profiles. A suitable tongued profile tooth 232 is taught in U.S. Pat. No. 5,968,049, the entire disclosure of which is incorporated by reference herein and relied upon. The tongued tooth 232 may either be serrated, as shown in U.S. Pat. No. 5,968,049, or non-serrated. Similarly, where the equatorial tooth 232 has a tongued profile (FIG. 3), it is as shown in U.S. Pat. No. 5,968,049.

In FIG. 1A, the tooth 32 is formed or results from bending the tooth 32 outward, leaving a flattened tooth with no side relief and rounded edges. In FIG. 2, the rounded tooth 132 is commonly known as a "cheese grater" tooth, manufactured with a high ram that is then later removed (FIG. 2A) to reveal a hemisphere with a cheese grater tooth-style at the edge.

Referring to FIGS. 1-3 and 5-7, the equatorial cutting site 28 presents a raised second tooth 32, 132, 232, 332 selected from squared 32 (FIG. 1), rounded 132 (FIGS, 2, 6-7), tongued 232 (FIG. 3) and bladed 332 (FIG. 5) profiles, Referring to FIGS. 1-7, the tool 10 has a hollow body 12 defining a domed shape with a rotational axis 14, an apex 16 aligned with the axis 14 and a hemispherical wall 18 extending from the apex 16 to an equatorial rim 20 spaced 90 degrees from the axis 14. The rim 20 has an edge 22 visible to the user that indicates the position of the tool 10 relative to the bone. A first plurality of cutting sites 24 is arrayed along the body 12 and a second plurality of cutting sites 28 is arrayed circumferentially along the edge 22. Preferably, the first plurality of cutting sites 24 present raised first teeth 30, 130, 230, 330 having a profile selected from squared 30, rounded 130, squared 230 and tongued 330 profiles. Also preferably, the second plurality of cutting sites 28 present raised second teeth 32, 132, 232, 332 selected from squared 32, rounded 132, tongued 232 and bladed 332 profiles. In FIGS. 1-3, body 12 is formed by starting with a hollow domed shape, with the wall 18 extending beyond the 90-degree equator (shown in phantom) and then cut. The equatorial teeth 32, 132, 232 are formed and wall 18 is then cut at the 90-degree equator so that the teeth are open on their lower side.

Referring to FIGS. 6-7, the tool 10 has a hollow body 12 defining a domed shape with a rotational axis 14, an apex 16 aligned with the axis 14 and a hemispherical wall 18 extending from the apex 16 to an equatorial rim 20 spaced 90 degrees from the axis 14. The rim 70 has an edge that is similar to the edge 22 shown in the embodiments in FIGS. 4 and 5. This edge is visible to the user to indicate the position of the tool 10 relative to the bone. A first plurality of cutting sites 24 is arrayed along the body 12 and a second plurality of cutting sites 28 is arrayed circumferentially along the edge 22 on downwardly depending lobes 36. The wall 18 continues past the equator of the tool 10 with the same radius of curvature as the rest of wall 18, rather than being made cylindrical at the equator. This continued curvature assures that the correct shape is being cut, even if the tool 10 is not advanced entirely in a linear fashion into the bone cavity being cut. Preferably, the first plurality of cutting sites 24 present raised first teeth 30, 130, 230, 330 having a profile selected from squared 30, rounded 130, squared 230 and tongued 330 profiles. Also preferably, the second plurality of cutting sites 28 present raised second teeth 32, 132 selected from squared 32 or rounded 132 profiles. The lobes 36 curve downwardly and inwardly, having the same curvature as the upper part of the wall 18 rather than being cylindrical in shape.

Figure 4:
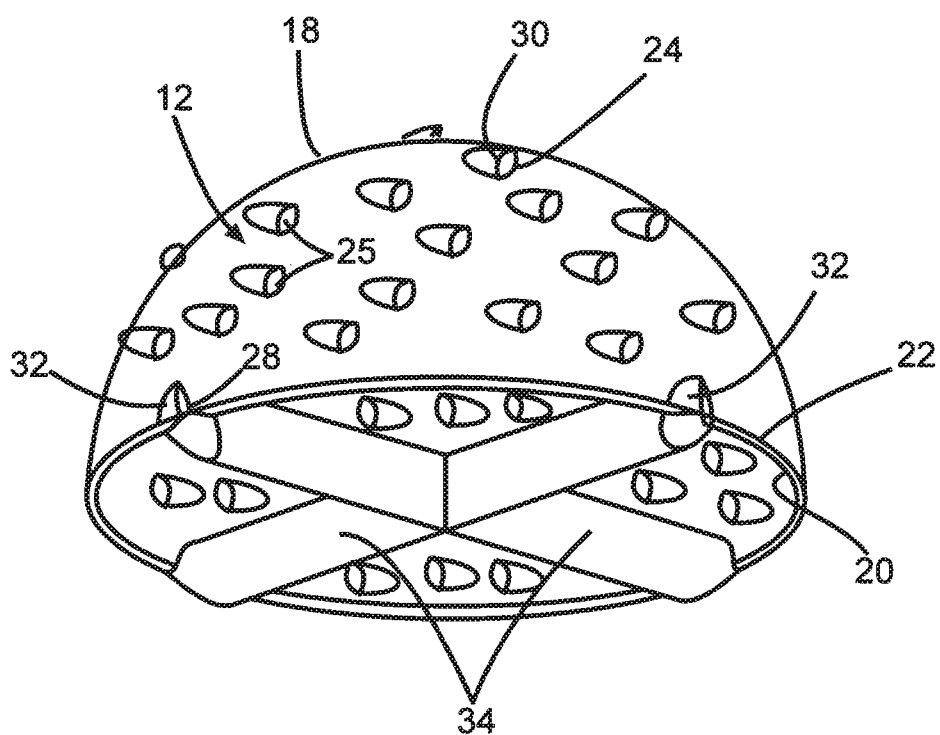
FIG. 4 is a perspective view of a preferred tool of the invention, showing a closed equatorial cutting site containing a flattened tooth profile.
Figure 5:
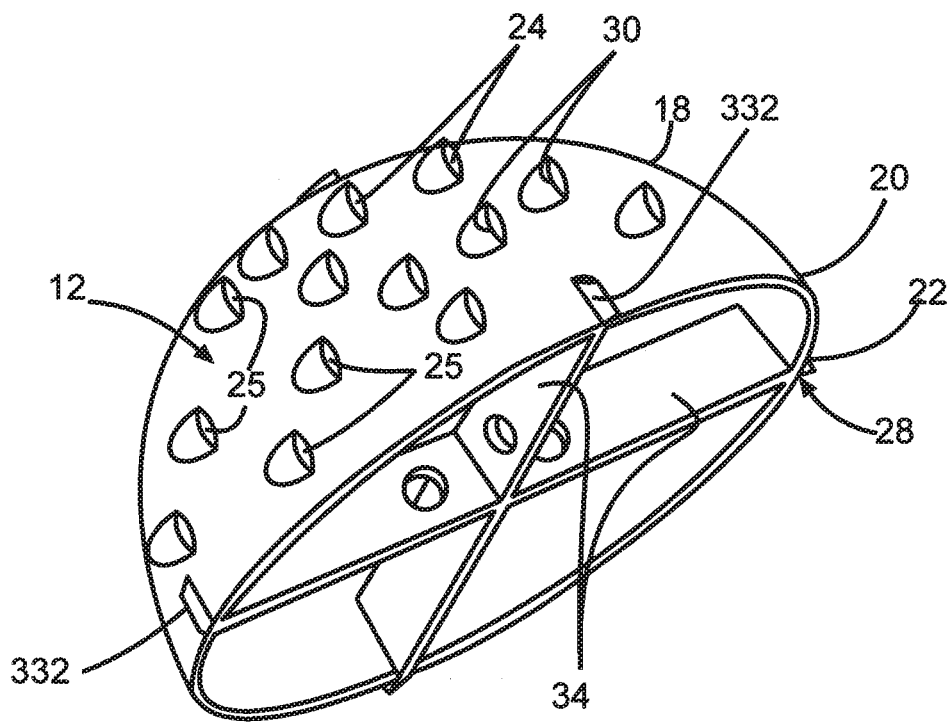
FIG. 5 is a perspective view of a preferred tool of the invention, showing closed equatorial cutting sites containing bladed teeth representing outboard extensions of the mounting bars.

Referring to FIGS. 4-5, the body 12 has at least one mounting bar 34 extending between the axis 14 and rim 20, with a tooth 32, 332 which, in FIG. 5 is an essentially contiguous radial projection or blade formed from the bar 34 outboard of the rim 20 along edge 22. The first plurality of cutting sites 24 preferably contains openings 25 for passage of debris, whereas the second plurality of sites 28 may be either open (FIGS. 1-2 and 6-7) or closed (FIGS. 4-5).

Preferably, the second plurality of teeth 32, 132, 232 are discontinuous, i.e., relieved on one side, with respect to the tool 10 shown in FIGS. 1-3, Teeth 32, 132, 232 are made discontinuous by cutting away the material of the body 12, shown in phantom (FIGS, 1-3) once the teeth are formed. Machining of the teeth 32, 132, 232 in body 12 is depicted in FIGS. 1A, 2A and 3A, respectively. By contrast, in FIGS. 6-7 the teeth 132 are continuous.

While one or more preferred embodiments of the present invention have been described, it should be understood that various changes, adaptations and modifications might be made without departing from the spirit of the invention and the scope of the appended claims.

What is claimed is:

1. A tool for cutting a hemispherical cavity in bone, the tool comprising:
a) a hollow, hemispherical wall portion of a dome extending along a rotational axis from an apex to an equatorial rim of the dome, wherein the rotational axis intersects the hemispherical wall portion at the apex, and wherein the equatorial rim is spaced from the rotational axis and resides on an imaginary equatorial plane aligned perpendicular to the rotational axis, wherein the hemispherical wall portion has a first outer radii measured from a focal point residing at where the rotational axis intersects with the imaginary equatorial plane;
b) at least one mounting bar extending perpendicular to the rotational axis and comprising spaced apart mounting bar ends secured to opposed locations of the hemispherical wall portion at the equatorial rim;
c) a plurality of first dome cutting teeth arrayed along the hemispherical wall portion; and
d) at least two second cutting teeth formed from respective ends of the at least one mounting bar outboard of the equatorial rim along an edge of the hemispherical wall portion thereby interrupting the hemispherical continuity of the equatorial rim with the at least two second cutting teeth,
e) wherein at least one of the first dome cutting teeth and at least one of the second cutting teeth are characterized as being wall portions of the hemispherical wall portion having been raised in an upwardly direction, and wherein each of the raised wall portions provides a dome cutting tooth sharp edge of a cutting radii spaced further from the focal point than the first outer radii of the hemispherical wall portion, and
f) wherein the plurality of the first dome cutting teeth face respective openings extending through the hemispherical wall portion for passage of debris into an interior of the hemispherical wall portion.

2. The tool of claim 1, wherein the plurality of the first dome cutting teeth have a profile selected from the group consisting of squared, rounded, tongued, and combinations thereof.

3. The tool of claim 1, wherein the sharp edge of at least one of the second cutting teeth has an edge profile selected from the group consisting of squared, rounded, tongued, bladed, and combinations thereof.

4. The tool of claim 1, wherein the at least one mounting bar comprises two mounting bars that intersect each other to form a cross.

5. The tool of claim 4, wherein ends of the two mounting bars are secured to locations that are spaced 90° from each other on the interior of the hemispherical wall portion.

6. The tool of claim 4, wherein the at least two second cutting teeth comprise four second cutting teeth, each being a second cutting tooth formed from a respective end of one of the two bars outboard of the rim along the edge of the hemispherical wall portion.

7. A tool for cutting a hemispherical cavity in bone, the tool comprising:
a) a hollow, hemispherical wall portion of a dome extending along a rotational axis from an apex to an equatorial rim of the dome, wherein the rotational axis intersects the hemispherical wall portion at the apex, and wherein the equatorial rim is spaced from the rotational axis and resides on an imaginary equatorial plane aligned perpendicular to the rotational axis, wherein the hemispherical wall portion has a first outer radii measured from a focal point residing at where the rotational axis intersects with the imaginary equatorial plane;
b) two mounting bars, each mounting bar extending perpendicular to the rotational axis and comprising spaced apart mounting bar ends secured to opposed locations of the hemispherical wall portion at the equatorial rim, wherein ends of the two mounting bars are secured to locations that are spaced 90° from each other on an interior of the hollow hemispherical wall portion;
c) a plurality of first dome cutting teeth arrayed along the hemispherical wall portion; and
d) four second cutting teeth, each second cutting tooth formed from a respective end of one of the two mounting bars outboard of the equatorial rim along an edge of the hemispherical wall portion thereby interrupting the hemispherical continuity of the equatorial rim with the four second cutting teeth, e) wherein at least one of the first dome cutting teeth and at least one of the second cutting teeth are characterized as being wall portions of the hemispherical wall portion having been raised in an upwardly direction, and wherein each of the raised wall portions provides a dome cutting tooth sharp edge of a cutting radii spaced further from the focal point than the first outer radii of the hemispherical wall portion, and f) wherein the plurality of the first dome cutting teeth face respective openings extending through the hemispherical wall portion for passage of debris into the interior of the hemispherical wall portion.

8. The tool of claim 7, wherein the plurality of the first dome cutting teeth have a profile selected from the group consisting of squared, rounded, tongued, and combinations thereof.

9. The tool of claim 7, wherein the sharp edge of at least one of the second cutting teeth has an edge profile selected from the group consisting of squared, rounded, tongued, bladed, and combinations thereof.

\* \* \* \* \*